(12) United States Patent
Crouch et al.

(10) Patent No.: US 11,612,668 B2
(45) Date of Patent: Mar. 28, 2023

(54) SOLAR-HEATED THERMO-CHEMICAL DECONTAMINATION SYSTEMS FOR FACEMASKS OR OTHER PERSONAL PROTECTION EQUIPMENT (PPE)

(71) Applicant: Raytheon Company, Waltham, MA (US)

(72) Inventors: David D. Crouch, Riverside, CA (US); David R. Sar, Marana, AZ (US); Alf L. Carroll, III, Marion, MA (US); John Carcone, Portsmouth, RI (US)

(73) Assignee: Raytheon Company, Waltham, MA (US)

( * ) Notice: Subject to any disclaimer, the term of this patent is extended or adjusted under 35 U.S.C. 154(b) by 407 days.

(21) Appl. No.: 16/986,761

(22) Filed: Aug. 6, 2020

(65) Prior Publication Data

US 2022/0040342 A1 Feb. 10, 2022

(51) Int. Cl.
*A61L 2/04* (2006.01)
*A61L 2/26* (2006.01)
*F24S 20/30* (2018.01)

(52) U.S. Cl.
CPC .................... *A61L 2/04* (2013.01); *A61L 2/26* (2013.01); *F24S 20/30* (2018.05); *A61L 2202/122* (2013.01); *A61L 2202/26* (2013.01)

(58) Field of Classification Search
CPC ..... A61L 2/04; A61L 2/07; A61L 2/16; A61L 2/20; A61L 2/208; A61L 2/26; A61L 2202/122; A61L 2202/26; F24S 20/30
See application file for complete search history.

(56) References Cited

U.S. PATENT DOCUMENTS

2009/0114210 A1* 5/2009 Guice .................. F24S 30/425
126/569

FOREIGN PATENT DOCUMENTS

| CN | 205569360 U | 9/2016 |
| CN | 108163387 A | 6/2018 |
| CN | 108207910 A | 6/2018 |
| WO | 2012012766 A2 | 1/2012 |

OTHER PUBLICATIONS

International Search Report and Written Opinion of the International Searching Authority dated Oct. 20, 2021 in connection with International Patent Application No. PCT/US2021/037168, 8 pages.
"Food Cooking Medical Sterilization and Ice Making (adsorption process) with the 'Soleil-Vapeur' Solar Thermal Steam Unit," soleil-vapeur.org, Oct. 2014, 4 pages.

* cited by examiner

*Primary Examiner* — Timothy C Cleveland

(57) ABSTRACT

A system includes a containment vessel configured to receive and hold one or more pieces of personal protection equipment to be heated and decontaminated during a decontamination process. The system also includes a solar collection device configured to heat the containment vessel based on received solar energy. The solar collection device includes a body having a first portion and a second portion. The first portion includes a solar aperture configured to receive the solar energy. The second portion is configured to receive the containment vessel within the body of the solar collection device. The solar collection device also includes louvered slats across the solar aperture. The louvered slats are configured to be rotated in order to control an amount of solar energy passing through the solar aperture into the body of the solar collection device.

6 Claims, 4 Drawing Sheets

SOLAR-HEATED THERMO-CHEMICAL DECONTAMINATION SYSTEMS FOR FACEMASKS OR OTHER PERSONAL PROTECTION EQUIPMENT (PPE)

TECHNICAL FIELD

This disclosure relates generally to medical decontamination devices and processes. More specifically, this disclosure relates to solar-heated thermo-chemical decontamination systems for facemasks or other personal protection equipment (PPE).

BACKGROUND

A dangerous gap has developed in the available supply of disposable facemasks, such as N95/N99/N100/P100 surgical masks, and other personal protection equipment (PPE), such as surgical gowns and booties, as a result of the COVID-19 pandemic. Accelerating demand has outstripped the ability of the supply chain to keep pace. As a result, medical staff are (among other things) routinely forced to wear the same mask or other personal protection equipment to treat multiple patients, which poses a cross-contamination hazard to patients and medical personnel. An additional risk is mask "breakthrough" in which contaminants eventually diffuse through the mask and infect the wearer.

SUMMARY

This disclosure provides solar-heated thermo-chemical decontamination systems for facemasks or other personal protection equipment (PPE).

In a first embodiment, a system includes a containment vessel configured to receive and hold one or more pieces of personal protection equipment to be heated and decontaminated during a decontamination process. The system also includes a solar collection device configured to heat the containment vessel based on received solar energy. The solar collection device includes a body having a first portion and a second portion. The first portion includes a solar aperture configured to receive the solar energy. The second portion is configured to receive the containment vessel within the body of the solar collection device. The solar collection device also includes louvered slats across the solar aperture. The louvered slats are configured to be rotated in order to control an amount of solar energy passing through the solar aperture into the body of the solar collection device.

In a second embodiment, an apparatus includes a solar collection device configured to heat a containment vessel based on received solar energy in order to decontaminate one or more pieces of personal protection equipment in the containment vessel. The solar collection device includes a body having a first portion and a second portion. The first portion includes a solar aperture configured to receive the solar energy. The second portion is configured to receive the containment vessel within the body of the solar collection device. The solar collection device also includes louvered slats across the solar aperture. The louvered slats are configured to be rotated in order to control an amount of solar energy passing through the solar aperture into the body of the solar collection device.

In a third embodiment, a method includes placing a containment vessel holding one or more pieces of personal protection equipment to be decontaminated into a solar collection device. The method also includes decontaminating the one or more pieces of personal protection equipment by heating the one or more pieces of personal protection equipment in the containment vessel using solar energy. The solar collection device includes a body having a first portion and a second portion. The first portion includes a solar aperture configured to receive the solar energy. The second portion is configured to receive the containment vessel within the body of the solar collection device. The solar collection device also includes louvered slats across the solar aperture. The louvered slats are configured to be rotated in order to control an amount of solar energy passing through the solar aperture into the body of the solar collection device.

Other technical features may be readily apparent to one skilled in the art from the following figures, descriptions, and claims.

BRIEF DESCRIPTION OF THE DRAWINGS

For a more complete understanding of this disclosure, reference is made to the following description, taken in conjunction with the accompanying drawings, in which.

DETAILED DESCRIPTION

Figure 1:
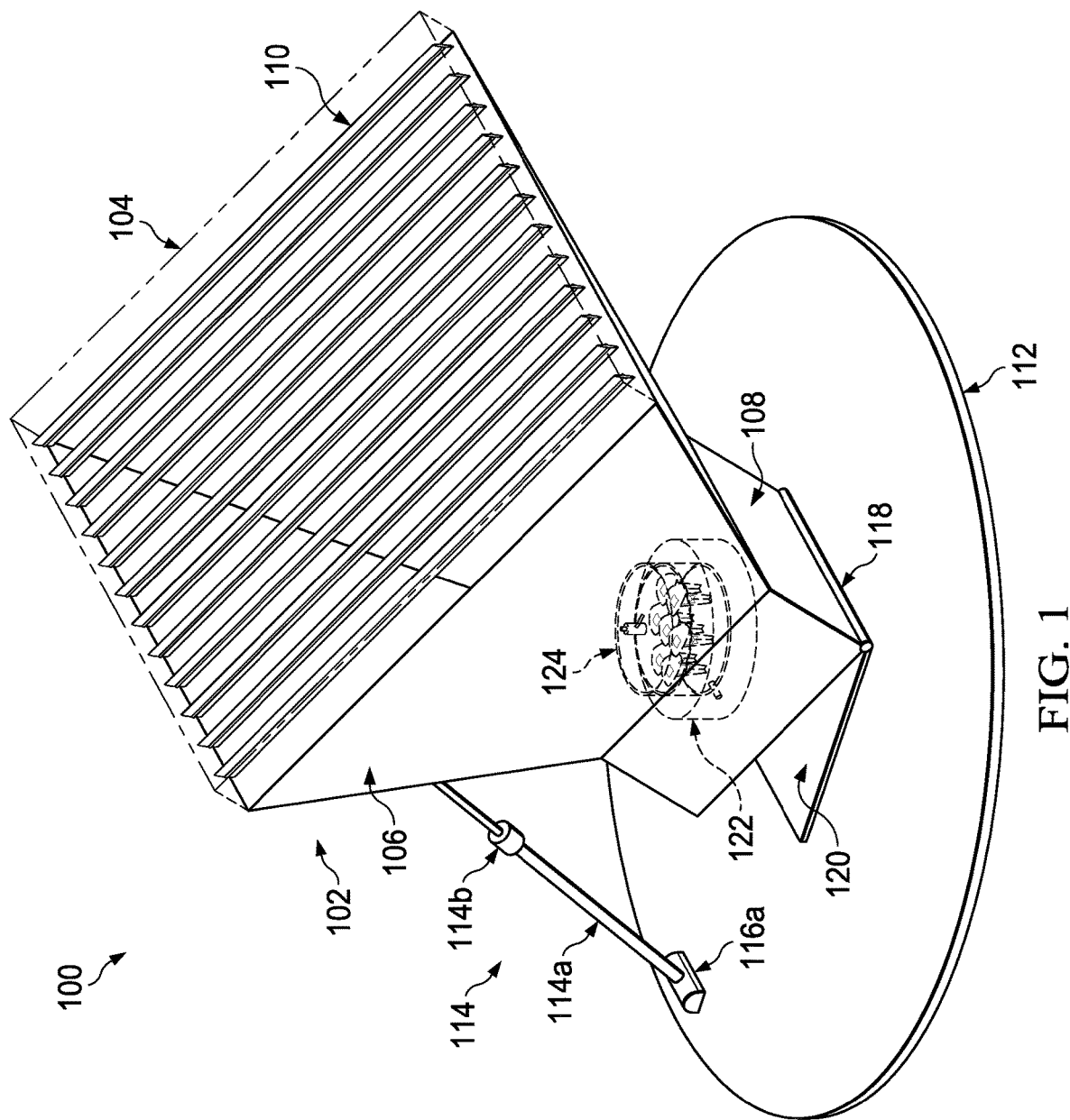
FIG. 1 illustrates a front perspective view of a solar-heated thermo-chemical decontamination system for facemasks or other personal protection equipment (PPE) in accordance with this disclosure.

FIGS. 1 through 4, described below, and the various embodiments used to describe the principles of the present disclosure are by way of illustration only and should not be construed in any way to limit the scope of the disclosure. Those skilled in the art will understand that the principles of the present disclosure may be implemented in any type of suitably arranged device or system.

As noted above, a dangerous gap has developed in the available supply of personal protection equipment (PPE), such as disposable facemasks (like N95/N99/N100/P100 surgical masks), surgical gowns, and booties, as a result of the COVID-19 pandemic. Disposable facemasks are sometimes referred to as surgical respirators. Accelerating demand has outstripped the ability of the supply chain to keep pace. As a result, medical staff are (among other things) routinely forced to wear the same mask or other personal protection equipment to treat multiple patients. This poses a cross-contamination hazard to patients and medical personnel and poses an additional risk related to mask "breakthrough" in which contaminants eventually diffuse through the mask and infect the wearer. This problem is particularly acute in developing nations, where sterile surgical masks and other personal protection equipment may be re-used as a matter of normal routine and where sterilization equipment or a stable and reliable power grid needed to operate the sterilization equipment may not exist.

Some approaches for decontaminating personal protection equipment involve using curved mirrors or solar-powered equipment to generate steam, which is then used to decontaminate the personal protection equipment. However, these approaches often require the use of specialized mirrors or equipment in large shipping containers to perform the decontamination. As a result, these approaches are often not easily deployable or maintainable.

This disclosure provides various solar-heated thermo-chemical decontamination systems for facemasks or other personal protection equipment. The decontamination systems use direct solar heating in a decontamination process, such as one that uses direct solar heating in combination with a low-concentration hydrogen peroxide solution, to rapidly decontaminate personal protection equipment in order to facilitate safe reuse of the equipment. Low-concentration hydrogen peroxide solutions (such as about 3% to 6%) are routinely available in a medical setting (such as a standard hospital or a mobile Army surgical hospital (MASH) setting) or in a commercial setting (such as a pharmacy or grocery store). Thus, various equipment and chemicals used to support the decontamination process are typically already available in the setting and can be used here. Moreover, as described below, peak temperatures experienced by the personal protection equipment during the decontamination process can be limited to a suitable range, such as about 65° C. to about 80° C., which prevents damage to the equipment or degradation of the equipment's fit or function. Further, the use of the decontamination systems may present little or no hazard to medical staff. In addition, the use of solar energy provides a more portable and more affordable mechanism for decontaminating facemasks or other personal protection equipment in various settings, such as in areas lacking conventional sterilization equipment or stable and reliable power grids.

In some embodiments, the process for decontaminating facemasks or other personal protection equipment involves placing the personal protection equipment within a containment vessel. The containment vessel may include at least one reservoir of a low-concentration hydrogen peroxide solution, such as an about 3% to about 6% hydrogen peroxide solution or other hydrogen peroxide solution that is safe for everyday use. The at least one reservoir may be positioned under the personal protection equipment to help provide adequate vapor in the containment vessel and around the personal protection equipment during decontamination. The personal protection equipment may also be soaked in the low-concentration hydrogen peroxide solution prior to placement in the containment vessel. The containment vessel can be initially heated and then sealed in order to keep moisture, hydrogen peroxide, and contaminants inside the containment vessel during the decontamination process. The containment vessel is heated via solar heating to a raised temperature, such as about 65° C. to about 80° C. (like about 70° C.), and maintained at the raised temperature for a relatively short period of time (like about five minutes to about ten minutes) to decontaminate the personal protection equipment inside the containment vessel. The combination of heat and heat-activated hydrogen peroxide deactivates or destroys biocontaminants faster and at a lower temperature than either heat or hydrogen peroxide vapor alone. Once the decontamination cycle is complete, the personal protection equipment can be dried (inside or outside the containment vessel) and then used as needed.

To support solar heating, the containment vessel is placed within a solar collection device that functions as a solar-powered oven, which uses direct solar heating to raise the temperature of the containment vessel and the personal protection equipment within the containment vessel. The solar collection device collects solar energy through a solar aperture, and a panel of blinds or slats over the solar aperture may be used to control the solar flux incident on the containment vessel, which may help to provide temperature control. The solar collection device may also include a turntable or other rotatable base that allows the solar collection device to be rotated around a vertical axis, which may help provide azimuth control. The solar collection device may further include a telescopic arm or other adjustment mechanism that allows the solar collection device to be tilted in a controllable manner, which may help provide elevation control. In addition, the solar collection device may include a hinged basket that can receive and hold the containment vessel, or the containment vessel itself may be hinged. The hinged feature allows the containment vessel to maintain a substantially horizontal orientation regardless of how the solar collection device is tilted, which helps prevent the personal protection equipment in the containment vessel from falling off stands or other structures or otherwise moving in an undesirable manner within the containment vessel.

In this way, synergy is achieved by attacking contaminants with both moist heating and hydrogen peroxide, yielding faster and more effective decontamination than either approach used alone. Also, the lower-temperature decontamination process protects facemasks or other personal protection equipment from damage or degradation, and the use of materials such as about 3% to about 6% hydrogen peroxide solution avoids toxic concentrations and potential explosiveness of higher concentrations. Moreover, the presence of metal nose strips, staples, or other metal components of the personal protection equipment will not cause damage to the equipment or their rubber straps during the decontamination process. This may be achieved using lower-temperature decontamination and the presence of moisture in the containment vessel, which helps to prevent the metal components from overheating and damaging the personal protection equipment. Further, a containment vessel (such as one with at least one pressure-relief valve) may optionally facilitate a multi-stage process, namely (i) a first stage where the pressure-relief valve is opened and where the containment vessel is heated so air within the containment vessel is substantially replaced by vapor, (ii) a second stage where the pressure-relief valve is closed, the containment vessel is sealed and heated, and water and hydrogen peroxide remain inside the containment vessel to maximize the speed and effectiveness of the decontamination, and (iii) a third stage where the pressure-relief valve is opened and where the containment vessel is heated so that water vapor and other vapor can escape while the personal protection equipment dries inside the containment vessel. This facilitates separate decontamination and drying operations, where water and hydrogen peroxide are retained during the decontamination and allowed to escape during the drying. In addition, at least one HEPA filter or other filter can be placed at the outlet(s) of the pressure-relief valve(s) or other outlet(s) of the containment vessel as an added precaution if necessary or desirable.

Figure 2:
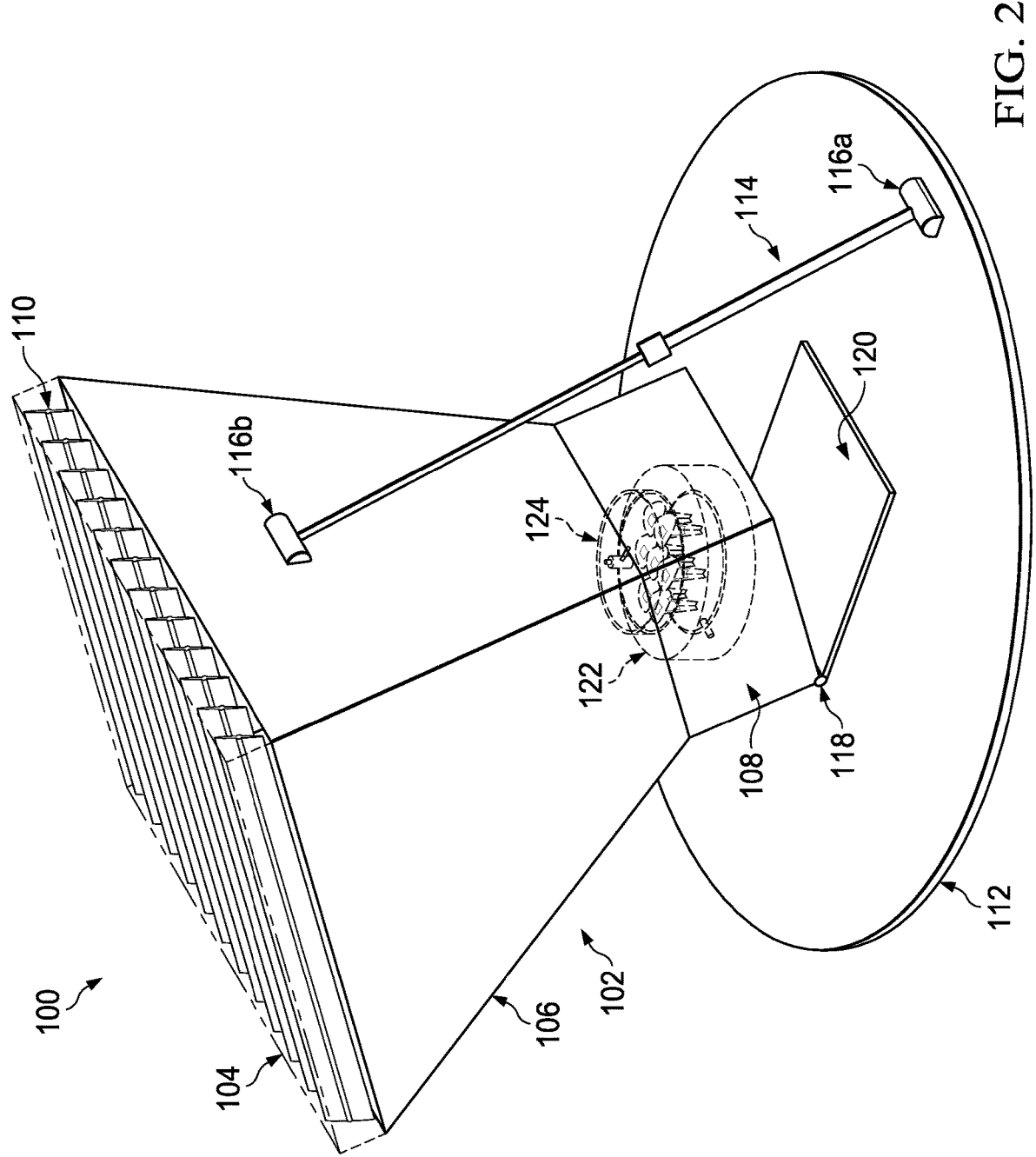
FIG. 2 illustrates a rear perspective view of the solar-heated thermo-chemical decontamination system for facemasks or other personal protection equipment in accordance with this disclosure.

FIG. 1 illustrates a front perspective view of a solar-heated thermo-chemical decontamination system 100 for facemasks or other personal protection equipment (PPE) in accordance with this disclosure. FIG. 2 illustrates a rear perspective view of the solar-heated thermo-chemical decontamination system 100 for facemasks or other personal protection equipment in accordance with this disclosure. As shown in FIGS. 1 and 2, the system 100 includes a solar collection device 102, which functions as a solar-powered oven. The solar collection device 102 here includes a solar aperture 104 through which solar energy can enter into an interior of the solar collection device 102. The solar collection device 102 also includes a body defined by a wider upper portion 106 and a narrower lower portion 108. The solar aperture 104 allows solar energy to enter into the solar collection device 102 and heat at least one object within the lower portion 108 of the solar collection device 102.

The solar aperture 104 includes any suitable opening through which solar energy can pass. In this example, the solar aperture 104 is generally rectangular or square, although the solar aperture 104 may have any other suitable shape. The upper portion 106 defines the solar aperture 104 and tapers from one end that defines the solar aperture 104 to the opposite end that meets the lower portion 108. The upper portion 106 here has four closed sides and two open ends (one end defining the solar aperture 104 and another end allowing passage of solar energy into the lower portion 108). In this example, the upper portion 106 has four sides defining a generally rectangular or square cross-sectional shape that increases in size moving up the upper portion 106 and that decreases in size moving down the upper portion 106, although the upper portion 106 may have any other suitable cross-sectional shape and number of sides. The lower portion 108 defines a space in which at least one object can reside and be heated. The lower portion 108 here has four closed sides, one closed end on bottom, and one open end on top (which allows passage of solar energy from the upper portion 106). In this example, the lower portion 108 has four sides defining a generally rectangular or square cross-sectional shape with a constant size moving up or down the lower portion 108, although the lower portion 108 may have any other suitable cross-sectional shape and number of sides.

The solar collection device 102 may be formed from any suitable material(s). For example, at least part of the solar collection device 102 may be formed from a highly-reflective material (such as one or more metals) that enable solar energy to be reflected into the lower portion 108 of the solar collection device 102. In some cases, the entire solar collection device 102 may be formed from a highly-reflective material, including outer surfaces and inner surfaces of the solar collection device 102. In other cases, the inner surfaces of the solar collection device 102 may be formed from a highly-reflective material, and the outer surfaces of the solar collection device 102 may be formed from an absorptive or other material. As a particular example, the entire solar collection device 102 may be formed from polished aluminum or other metal, and the outer surfaces of the solar collection device 102 may or may not be covered by paint or other material. As another particular example, the solar collection device 102 may be formed from ruggedized plastic or other material, and reflective foil or other reflective material may be placed on at least inner surfaces of the solar collection device 102 (and the reflective foil or other reflective material may or may not be replaceable).

The solar collection device 102 may also be formed in any suitable manner, such as additive manufacturing, injection molding, casting, machining, or other suitable technique. The manufacturing technique used to fabricate the solar collection device 102 can vary based on, among other things, the material(s) being used to form the solar collection device 102. The solar collection device 102 may have any suitable size, shape, and dimensions. In addition, while all sides of the solar collection device 102 are shown here as being generally flat, this need not be the case.

Depending on the implementation, it is possible for solar ovens using reflectors to reach relatively high temperatures, such as about 200° C. or more. In order to provide some form of temperature control, the solar collection device 102 here includes louvered slats 110 (which are sometimes referred to as louvered doors) that extend across the solar aperture 104 of the solar collection device 102. The slats 110 can be rotated to selectively allow more or less solar energy to enter into the solar collection device 102, thereby controlling the solar flux that is incident on at least one object within the solar collection device 102. Thus, the angle(s) of the slats 110 can be varied to control the amount of solar energy that passes into the solar collection device 102. Note that the number and size of the slats 110 can vary as needed or desired. Also note that the slats 110 may each be rotated independent of the other slats 110, or one or more connecting bars may couple one or more ends of the slats 110 together so that rotation of one slat 110 causes a corresponding rotation of the other slats 110. In addition, note that the slats 110 may be adjusted manually or in an automated manner, such as through the use of servos or other actuators that are controlled via a feedback loop tied to a temperature monitor.

Each slat 110 may be formed from any suitable material(s). In some embodiments, for example, the slats 110 may be formed from a diffuse reflecting material that reflects solar energy in a non-focused manner. In other embodiments, the slats 110 may be formed of or coated with an absorptive material that absorbs solar energy. Each slat 110 may also be formed in any suitable manner, such as additive manufacturing, injection molding, casting, machining, or other suitable technique. In addition, each slat 110 may have any suitable size, shape, and dimensions. In some cases, the slats 110 may be sized to completely or substantially block all solar energy from entering the solar collection device 102 when rotated to a substantially traverse position across the solar aperture 104.

Because the position of the sun obviously changes throughout the day, the solar collection device 102 can be aimed at different positions of the sky depending on the sun's position. To facilitate this aiming, the solar collection device 102 in this example is used in conjunction with a base 112 and a telescopic arm 114. The base 112 may represent a turntable or other suitable structure that can be rotated, which may allow for azimuth adjustments to be made to the solar collection device 102. Note, however, that the base 112 may also represent a fixed base that can simply be rotated or otherwise moved manually. The base 112 may be formed from any suitable material(s), such as metal or ruggedized plastic. The base 112 may also be formed in any suitable manner, such as additive manufacturing, injection molding, casting, machining, or other suitable technique. In addition, the base 112 may have any suitable size, shape, and dimensions. In this example, the base 112 is generally circular and is wider than the solar collection device 102, although other shapes and sizes may be used for the base 112.

The telescopic arm 114 extends between the solar collection device 102 and the base 112. The telescopic arm 114 can be extended (lengthened) and retracted (shortened) in order to control the tilt of the solar collection device 102 relative to the base 112, which may allow for elevation adjustments to be made to the solar collection device 102. Mounts 116a-116b respectively couple the telescopic arm 114 to the base 112 and the solar collection device 102 and allow for rotational movement of the telescopic arm 114. The telescopic arm 114 includes any suitable structure configured to adjust a tilt of the solar collection device 102. In this particular example, the telescopic arm 114 includes multiple rods 114a and a locking nut 114b. One rod 114a may fit and move within another rod 114a to provide an adjustable overall length of the telescopic arm 114, and the locking nut 114b can secure the rods 114a together to hold the length of the telescopic arm 114. The telescopic arm 114 may be formed from any suitable material(s) and in any suitable manner. Each mount 116a-116b includes any suitable structure configured to secure the telescopic arm 114 to another structure. For instance, each mount 116a-116b may represent a housing with a pin that extends through the telescopic arm 114. Each mount 116a-116b may be formed from any suitable material(s) and in any suitable manner.

Note that the base 112 and telescopic arm 114 have been described above as being used to allow for azimuth and elevation control of the solar collection device 102. The combination of these two controls allow for pointing the solar aperture 104 directly at the sun at any point in the sky up to maximum declination. However, it should be noted that any other suitable mechanism(s) may be used to point the solar collection device 102 and to hold the solar collection device 102 in a desired orientation. Also note that azimuth and elevation control (or other control) may occur manually or in an automated manner, such as through the use of a clock drive (like one similar to those used with telescopes to maintain alignment with the sun).

In this example, the solar collection device 102 is coupled to the base 112 using at least one hinge 118 and a plate 120. The hinge 118 allows the solar collection device 102 to be tilted using the telescopic arm 114 while the solar collection device 102 is coupled to the base 112. The hinge 118 includes any suitable structure configured to allow rotational movement of the solar collection device 102 relative to the base 112. The plate 120 may optionally be coupled to the hinge 118 and the base 112, thereby helping to secure the solar collection device 102 to the base 112. In some cases, the plate 120 may be sized and shaped to fit within a recess in the bottom surface of the lower portion 108, or the lower portion 108 may be designed to sit on the plate 120. The plate 120 may be formed from any suitable material(s) and in any suitable manner. The plate 120 is described as being optional here since the solar collection device 102 may be coupled directly to the base 112 via the hinge 118 without use of the plate 120.

Shown within the solar collection device 102 is a basket or other holder 122 and a containment vessel 124. The holder 122 is designed to receive and hold the containment vessel 124. The holder 122 functions as a gimbal to allow the containment vessel 124 to remain substantially level during tilting of the solar collection device 102. The containment vessel 124 contains one or more facemasks or other pieces of personal protection equipment to be decontaminated using heating provided by the solar collection device 102. The personal protection equipment may include one or more facemasks, such as N95, N99, N100, or P100 surgical masks, or other personal protection equipment.

The holder 122 includes any suitable structure configured to substantially maintain a desired orientation of a containment vessel 124, such as a basket coupled to the solar collection device 102 by pins. Note, however, that use of the holder 122 is optional since the containment vessel 124 itself may include pins or other structures that allow rotational motion of the containment vessel 124 relative to the solar collection device 102, which can help maintain a desired orientation of the containment vessel 124 in the solar collection device 102. However implemented, the "self-leveling" feature provided by the holder 122 or containment vessel 124 can help to prevent undesired movement of the personal protection equipment within the containment vessel 124. As a result, there may be little or no need for the containment vessel 124 to include restraints to secure the personal protection equipment within the containment vessel 124 (although such constraints may be used).

Figure 3:
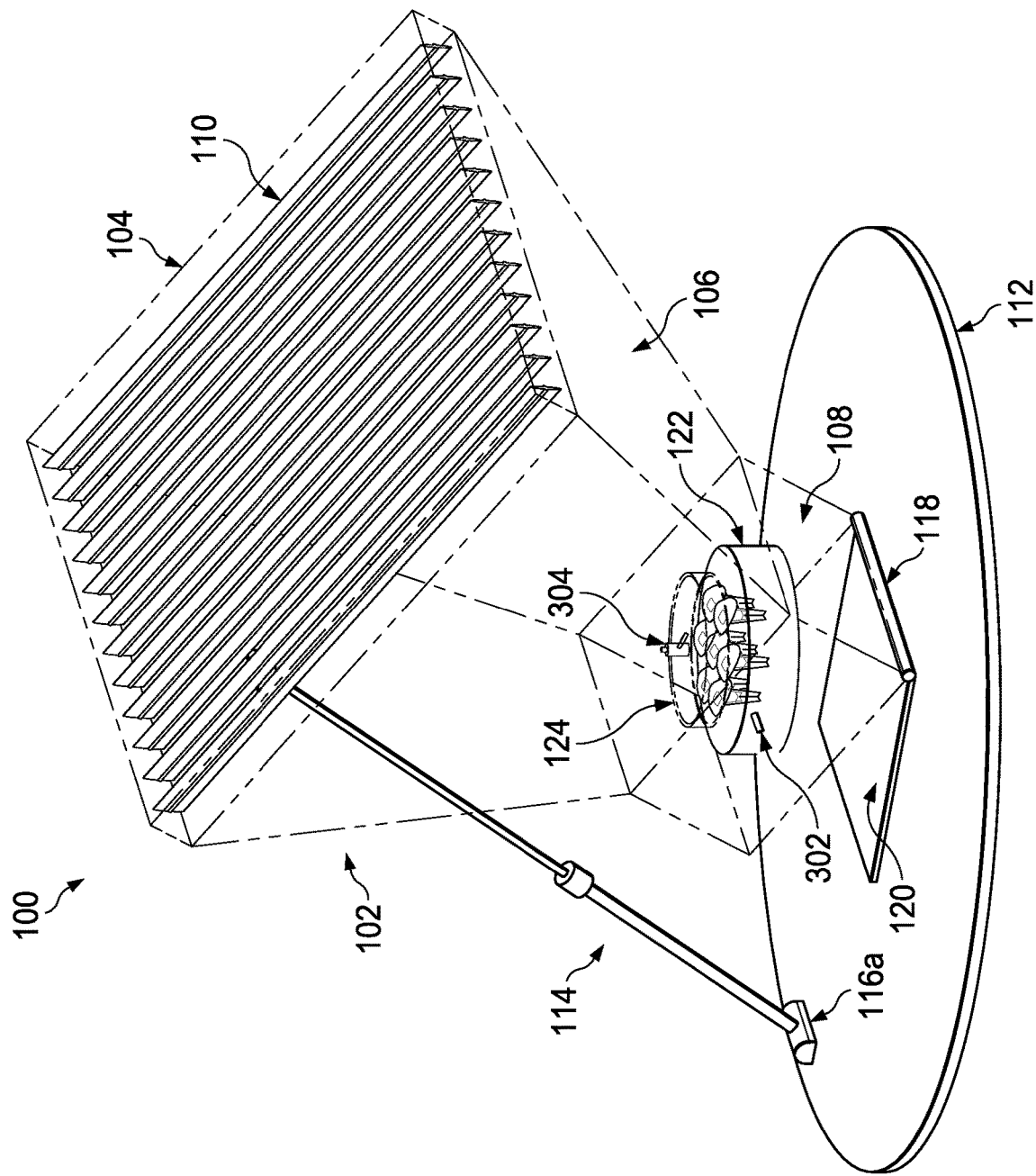
FIG. 3 illustrates a front perspective view of the solar-heated thermo-chemical decontamination system for facemasks or other personal protection equipment with internal components visible in accordance with this disclosure.
Figure 4:
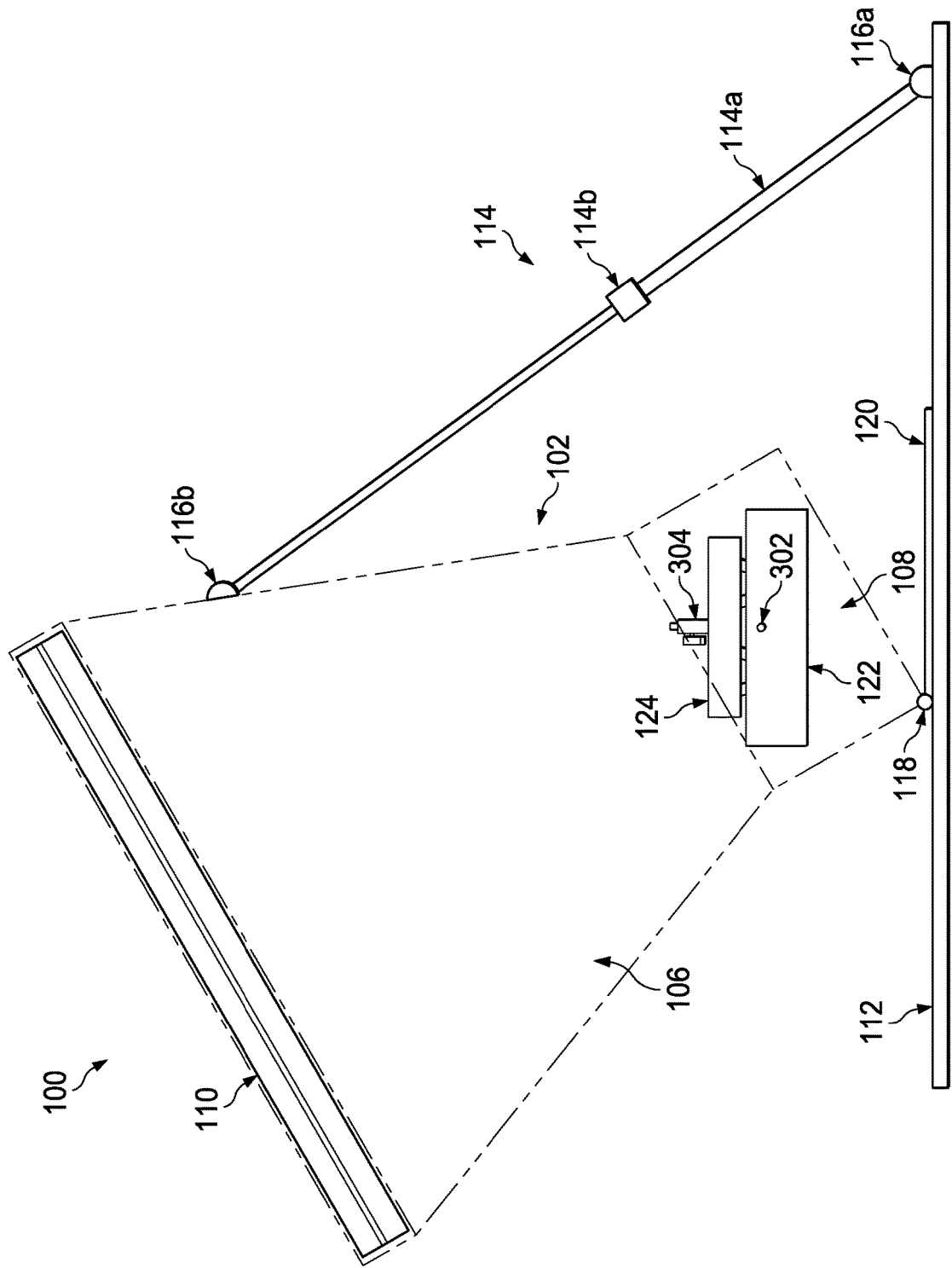
FIG. 4 illustrates a side view of the solar-heated thermo-chemical decontamination system for facemasks or other personal protection equipment with internal components visible in accordance with this disclosure.

FIG. 3 illustrates a front perspective view of the solar-heated thermo-chemical decontamination system 100 for facemasks or other personal protection equipment with internal components visible in accordance with this disclosure. FIG. 4 illustrates a side view of the solar-heated thermo-chemical decontamination system 100 for facemasks or other personal protection equipment with internal components visible in accordance with this disclosure. In particular, FIGS. 3 and 4 illustrate additional details regarding the holder 122 and containment vessel 124 within the lower portion 108 of the solar collection device 102.

As shown in FIGS. 3 and 4, the holder 122 represents a structure that is configured to receive and hold the containment vessel 124. In this example, the holder 122 is generally in the form of a cylindrical basket, although the holder 122 may have any other suitable form. The holder 122 is coupled to the lower portion of 108 of the solar collection device 102 in such a manner to allow for rotation, such as by using multiple pins 302. The pins 302 may be attached near the top of the holder 122 so that gravity causes the holder 122 (and therefore the containment vessel 124) to rotate as the solar collection device 102 is tilted. Ideally, this helps keep the containment vessel 124 substantially level. In some cases, the holder 122 may have a size and shape that closely complements the size and shape of the containment vessel 124, such as when the containment vessel 124 fits snuggly within the holder 122. In other cases, the holder 122 may be designed to allow the holder 122 to receive containment vessels 124 of various shapes and sizes.

The containment vessel 124 may optionally include at least one pressure-relief valve 304. The pressure-relief valve 304 includes any suitable structure configured to be selectively opened and closed to provide or block a pathway for pressure to escape from an interior volume of the containment vessel 124. The pressure-relief valve 304 allows the interior volume of the containment vessel 124 to be sealed during heating of the personal protection equipment, thereby increasing the pressure within the containment vessel 124 during the heating. Among other things, this helps to keep hydrogen peroxide vapor surrounding the personal protection equipment during a decontamination process. Once the decontamination process is completed, the pressure-relief valve 304 can be opened in order to allow excess pressure in the containment vessel 124 to be relieved. At that point, the personal protection equipment can be removed from the containment vessel 124 for drying, or the containment vessel 124 can be reheated (with the pressure-relief valve 304 opened) to dry the personal protection equipment.

In some cases, the pressure-relief valve 304 may include an integrated filter or otherwise be used in conjunction with a filter. The filter may be used to filter air or other fluid passing out of the containment vessel 124, such as during or after heating of the containment vessel 124. For instance, after being heated for a specified period of time, the pressure-relief valve 304 may be opened, and the filter may filter air passing out of the containment vessel 124. Among other things, this may help to prevent contamination of air or nearby surfaces during use of the containment vessel 124.

Each filter includes any suitable structure configured to remove contaminants or other materials from fluid, such as a HEPA filter.

Note that this example includes a single pressure-relief valve 304, although the containment vessel 124 may include more than one pressure-relief valve 304. Also note that the one or more pressure-relief valves 304 may be positioned at any suitable location(s) of the containment vessel 124 and may or may not be positioned on top of the containment vessel 124. Further note that the use of integrated filters and pressure-relief valves is not required and that, for instance, at least one pressure-relief valve and at least one separate filter may be used (or the filter or filters may be omitted completely). In addition, note that the use of the pressure-relief valves is optional and not required.

The specific structure of the containment vessel 124 used in the system 100 can vary in any number of ways, and this disclosure is not limited to any particular type of containment vessel 124. In general, the containment vessel 124 may represent any suitable structure configured to hold one or more pieces of personal protection equipment and to be heated using solar energy in the solar collection device 102. Some examples of possible designs for the containment vessel 124 may be found in U.S. Provisional Patent Application Ser. No. 63/015,000 filed on Apr. 24, 2020 and U.S. patent application Ser. No. 16/944,617 filed on Jul. 31, 2020 (both of which are hereby incorporated by reference in their entirety). However, other designs for the containment vessel 124 may be used in the solar collection device 102, and this disclosure is not limited to any specific design of the containment vessel 124. For instance, standard pressure cookers or other conventional devices that can be sealed and heated may be used here as the containment vessel 124.

In some embodiments, a decontamination process involving the system 100 may occur as follows. A suitable amount of liquid, such as low-concentration (like 3% to 6%) hydrogen peroxide solution, can be placed inside the containment vessel 124. Also, a suitable amount of personal protection equipment can be placed inside the containment vessel 124, such as an amount of personal protection equipment that partially or substantially fills the interior space of the containment vessel 124. The personal protection equipment may or may not have been previously soaked in liquid, such as a low-concentration hydrogen peroxide solution. A lid of the containment vessel 124 can be secured to a body of the containment vessel 124 to enclose the personal protection equipment within the containment vessel 124, and the containment vessel 124 can be placed in the holder 122 or otherwise secured within the lower portion 108 of the solar collection device 102.

The solar aperture 104 of the solar collection device 102 can be pointed directly or otherwise at the sun, and heating of the containment vessel 124 occurs. The pressure-relief valve(s) 304 may initially be opened to allow air in the containment vessel 124 to be substantially replaced with vapor, and the pressure-relief valve(s) 304 may then be closed. The heating may then continue for a specified time period. For example, the heating can heat the personal protection equipment to a temperature within a relatively-low temperature range, such as about 65° C. to about 80° C., to prevent damage to the personal protection equipment. The personal protection equipment can remain within the about 65° C. to about 80° C. temperature range for between about five minutes to about ten minutes. During this time, the combination of the heat and the vaporized hydrogen peroxide can help to decontaminate the personal protection equipment in the containment vessel 124.

Once this part of the process is completed, the personal protection equipment can be dried, which may occur in any suitable manner. For instance, in some cases, the personal protection equipment may be removed from the containment vessel 124 and allowed to air dry (such as on a rack), or the personal protection equipment may be removed from the containment vessel 124 and mechanically dried using a hair dryer or other heat or air source. In other cases, at least one pressure-relief valve 304 of the containment vessel 124 may be opened, and the containment vessel 124 can again be heated (possibly in the same or similar manner as the first heating) so that moisture within the containment vessel 124 can escape and allow drying of the personal protection equipment. At least one filter (such as at least one HEPA filter) may be integrated with or otherwise used with the pressure-relief valve(s) 304 to filter material passing through the pressure-relief valve(s) 304. Any other suitable approach for drying the personal protection equipment may also be used here.

In some embodiments, the solar collection device 102 may be portable and therefore designed and constructed so as to be easily assembled/disassembled and transported. For example, joints between different surfaces of the solar collection device 102 may be hinged so that the solar collection device 102 can be collapsed into a more portable or storable form. As another example, different surfaces of the solar collection device 102 may be designed to be coupled to and uncoupled from each other, such as when various surfaces of the solar collection device 102 include cylindrical or other projections designed to be inserted into slots of other surfaces of the solar collection device 102. In general, the solar collection device 102 may be designed to have any desired integral or separable components.

Also, in some embodiments, the solar collection device 102 or the containment vessel 124 may be designed to include some form of visual indicator to help identify the temperature or other characteristics of the containment vessel 124. For example, a thermometer may be used inside the solar collection device 102 or on the containment vessel 124 to identify a temperature of the containment vessel 124. This may allow a user to make manual adjustments to the slats 110 or the direction of the solar collection device 102 to help ensure that the containment vessel 124 reaches a suitable temperature or temperature range without overheating the personal protection equipment. As another example, a temperature sensor and readout may be an integral part of the containment vessel 124 or a part of the system 100 that is attached to the containment vessel 124 prior to decontamination. As yet another example, a pop-up thermometer or other indicator (such as one similar to those used in turkeys to indicate when cooking is completed) may be incorporated into the containment vessel 124, and a red plastic cap or other component protrudes above the surface of the containment vessel 124 when the desired temperature and time have been reached and decontamination has been completed. However, heating may occur without any visual or other feedback.

Although FIGS. 1 through 4 illustrate various views of one example embodiment of a solar-heated thermo-chemical decontamination system 100 for facemasks or other personal protection equipment, various changes may be made to FIG. 1 through 4. For example, the sizes, shapes, and dimensions of various components in the system 100 can vary as needed or desired. Also, the number and placement of various components in the system 100 can vary as needed or desired.

In addition, the system 100 may be used in any other suitable decontamination process and is not limited to the specific processes described above.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A method comprising:
   placing a containment vessel holding one or more pieces of personal protection equipment to be decontaminated into a solar collection device; and
   decontaminating the one or more pieces of personal protection equipment by heating the one or more pieces of personal protection equipment in the containment vessel using solar energy;
   wherein the solar collection device comprises:
      a body comprising a first portion and a second portion, the first portion comprising a solar aperture configured to receive the solar energy, the second portion configured to receive the containment vessel within the body of the solar collection device; and
      louvered slats across the solar aperture, the louvered slats configured to be rotated in order to control an amount of solar energy passing through the solar aperture into the body of the solar collection device.

2. The method of claim 1, wherein the solar collection device further comprises:
   a base coupled to the solar collection device; and
   a hinge configured to permit tilting of the solar collection device on the base.

3. The method of claim 2, further comprising:
   adjusting the tilt of the solar collection device relative to the base using a telescopic arm coupling the solar collection device and the base, the telescopic arm configured to be controllably lengthened and shortened.

4. The method of claim 3, further comprising:
   rotating the base to provide azimuth control for the solar collection device; and
   controlling the telescopic arm to provide elevation control for the solar collection device.

5. The method of claim 2, further comprising:
   placing the containment vessel in a holder coupled to the second portion of the solar collection device, the holder configured to rotate as the solar collection device is tilted to maintain the containment vessel in a substantially level orientation.

6. The method of claim 1, further comprising:
   adjusting the louvered slats to provide temperature control for the containment vessel within the solar collection device.

* * * * *